(12) United States Patent
He et al.

(10) Patent No.: US 12,346,999 B2
(45) Date of Patent: Jul. 1, 2025

(54) DATA PROCESSING METHOD, APPARATUS, DEVICE AND STORAGE MEDIUM

(71) Applicant: Wuxi Hisky Medical Technologies Co., Ltd., Wuxi (CN)

(72) Inventors: Qiong He, Wuxi (CN); Xiaochen Xu, Wuxi (CN); Jinhua Shao, Wuxi (CN); Jin Sun, Wuxi (CN); Houli Duan, Wuxi (CN)

(73) Assignee: Wuxi Hisky Medical Technologies Co., Ltd., Wuxi (CN)

( * ) Notice: Subject to any disclaimer, the term of this patent is extended or adjusted under 35 U.S.C. 154(b) by 488 days.

(21) Appl. No.: 17/586,566

(22) Filed: Jan. 27, 2022

(65) Prior Publication Data
US 2022/0148238 A1 May 12, 2022

Related U.S. Application Data

(63) Continuation of application No. PCT/CN2020/105006, filed on Jul. 28, 2020.

(30) Foreign Application Priority Data

Aug. 1, 2019 (CN) .......................... 201910706620.X

(51) Int. Cl.
*G06T 11/00* (2006.01)
*G06V 10/40* (2022.01)

(52) U.S. Cl.
CPC ............ *G06T 11/008* (2013.01); *G06V 10/40* (2022.01); *G06T 2207/10132* (2013.01)

(58) Field of Classification Search
CPC ......... A61B 8/06; A61B 8/485; A61B 8/5207; A61B 8/5215; A61B 8/5269;
(Continued)

(56) References Cited

U.S. PATENT DOCUMENTS

2002/0045822 A1 4/2002 Powers
2010/0312112 A1 12/2010 Kamiyama
(Continued)

FOREIGN PATENT DOCUMENTS

CN 102579071 A 7/2012
CN 103164599 A 6/2013
(Continued)

OTHER PUBLICATIONS

Extended European Search Report of the parallel application EP20846593.0.
(Continued)

*Primary Examiner* — Zhiyu Lu
(74) *Attorney, Agent, or Firm* — J.C. PATENTS

(57) ABSTRACT

A data processing method and apparatus, a device and a storage medium, where the method includes: obtaining first target result data according to an original ultrasonic echo signal, where the first target result data includes a related parameter of a detected object; performing feature extraction on the first target result data using a pre-trained feature extraction model to obtain second target result data; and performing corresponding processing on the detected object based on the second target result data. By performing feature extraction on the related parameter of the detected object using the pre-trained feature extraction model to obtain the second target result data, and further performing corresponding processing on the detected object based on the second target result data, thereby improving accuracy of judging the state of the detected object effectively.

14 Claims, 4 Drawing Sheets

(58) Field of Classification Search
CPC ......... G06T 11/008; G06T 2207/10132; G01S 7/52028; G01S 7/52036; G06V 10/40
See application file for complete search history.

(56) References Cited

U.S. PATENT DOCUMENTS

| | | |
|---|---|---|
| 2011/0319756 A1 | 12/2011 | Zheng |
| 2012/0271144 A1 | 10/2012 | Kim |
| 2013/0245442 A1 | 9/2013 | Hazard |
| 2013/0303913 A1* | 11/2013 | Tian .................... G01S 15/8993 600/447 |
| 2013/0317361 A1 | 11/2013 | Tabaru |
| 2013/0317362 A1 | 11/2013 | Shi |
| 2016/0143617 A1 | 5/2016 | Ebbini |
| 2017/0270664 A1 | 9/2017 | Hoogi |
| 2020/0281662 A1* | 9/2020 | Cong .................... A61B 8/481 |

FOREIGN PATENT DOCUMENTS

| | | |
|---|---|---|
| CN | 103784166 A | 5/2014 |
| CN | 104380134 A | 2/2015 |
| CN | 104983442 A | 10/2015 |
| CN | 105872046 A | 8/2016 |
| CN | 106361376 A | 2/2017 |
| CN | 107582097 A | 1/2018 |
| CN | 107661121 A | 2/2018 |
| CN | 108095763 A | 6/2018 |
| CN | 108268897 A | 7/2018 |
| CN | 110313941 A | 10/2019 |
| EP | 3066985 A1 | 9/2016 |
| JP | 2013146625 A | 8/2013 |
| JP | 2015136467 A | 7/2015 |
| WO | WO9824065 A1 | 6/1998 |
| WO | WO199824065 A1 | 6/1998 |
| WO | WO2011034005 A1 | 3/2011 |
| WO | WO2011085469 A1 | 7/2011 |
| WO | WO2015029651 A1 | 3/2015 |
| WO | WO2017222970 A1 | 12/2017 |
| WO | WO2019086365 A1 | 5/2019 |

OTHER PUBLICATIONS

First Office Action of the parallel application IN202217005160.
First Office Action of the parallel application RU2022104992.
First Office Action of the parallel application JP2022-506450.
Second Office Action of the parallel application RU2022104992.
International Search Report of PCT/CN2020/105006.
First Office Action of priority application CN201910706620X.
Second Office Action of priority application CN201910706620X.
NPL: Title: Ultrasound imaging equipment, Publisher: Medical Imaging Equipment Medical Devices Section, Author: State Food and Drug Administration Personnel Department State Food and Drug Administration Advanced Training Institute Publication Date: Oct. 31, 2010.
Notice of Allowance of priority application CN201910706620X.
Second Office Action of the parallel application AU2020322893.
Notice of Allowance of the parallel application KR10-2022-7003657.

* cited by examiner

DATA PROCESSING METHOD, APPARATUS, DEVICE AND STORAGE MEDIUM

CROSS-REFERENCE TO RELATED APPLICATIONS

This application is a continuation of International Application No. PCT/CN2020/105006, filed on Jul. 28, 2020, which claims priority to Chinese Patent Application No. 201910706620.X, filed on Aug. 1, 2019, both of the applications are hereby incorporated by reference in their entireties.

TECHNICAL FIELD

The present application relates to the technical field of ultrasound image processing and, in particular, to a data processing method and apparatus, a device and a storage medium.

BACKGROUND

With the advancement of science and technology, ultrasound imaging technology is widely used in various fields. In prior art, in general, after an original ultrasonic echo signal is acquired, it is necessary to perform image reconstruction and image processing to obtain some related parameters of a detected object, such as a velocity, a direction, etc., and judge a state of the detected object according to these related parameters.

However, accuracy of judging the state of the detected object in the prior art is relatively low, which gradually cannot meet an accuracy requirement for ultrasonic detection of the detected object. Therefore, how to accurately judge the state of the detected object has become a technical problem that needs to be solved urgently.

SUMMARY

The present application provides a data processing method and apparatus, a device, and a storage medium to solve disadvantages of low judgment accuracy in the prior art A first aspect of the present application provides a data processing method, including:
obtaining first target result data according to an original ultrasonic echo signal, where the first target result data includes a related parameter of a detected object;
performing feature extraction on the first target result data using a pre-trained feature extraction model to obtain second target result data; and
performing corresponding processing on the detected object based on the second target result data.

A second aspect of the present application provides a data processing apparatus, including:
a first processing module, configured to obtain first target result data according to an original ultrasonic echo signal, where the first target result data includes a related parameter of a detected object;
a second processing module, configured to perform feature extraction on the first target result data using a pre-trained feature extraction model to obtain second target result data; and
a third processing module, configured to perform corresponding processing on the detected object based on the second target result data.

A third aspect of the present application provides a computer device, including: at least one processor and a memory;
where the memory stores a computer program; and the at least one processor executes the computer program stored in the memory to implement the method provided in the first aspect.

A fourth aspect of the present application provides a computer-readable storage medium in which a computer program is stored, and the method provided in the first aspect is implemented when the computer program is executed.

According to the data processing method and apparatus, device, and storage medium provided in the present application, by performing feature extraction on a related parameter of a detected object using a pre-trained feature extraction model to obtain second target result data, and further performing corresponding processing on the detected object based on the second target result data, accuracy of judging the state of the detected object can be improved effectively.

BRIEF DESCRIPTION OF THE DRAWINGS

In order to more clearly describe the technical solution in embodiments of the present application or the prior art, in the following, the drawings that need to be used in the description of the embodiments or the prior art will be introduced briefly. Apparently, the drawings in the following description are a part of embodiments of the present application. For persons of ordinary skill in the art, other drawings can be obtained based on these drawings without paying creative labor.

Through the above drawings, specific embodiments of the present application have been shown, which will be described in more detail below. These drawings and descriptions are not intended to limit the scope of the concept of the present disclosure in any way, but to explain the concept of the present application to the persons skilled in the art by referring to specific embodiments.

DESCRIPTION OF EMBODIMENTS

In order to make the purpose, the technical solution, and the advantage of embodiments of the present application clearer, the technical solution in embodiments of the present application will be clearly and completely described below with reference to the accompanying drawings. Apparently, the described embodiments are merely a part rather than all embodiments of the present application. All other embodiments obtained by the persons of ordinary skill in the art based on embodiments in the present application without paying creative labor shall fall within the protection scope of the present application.

Firstly, terms involved in the present application will be explained.

Image reconstruction refers to the technology of obtaining shape information of a three-dimensional object through digital processing of data measured outside of an object. Image reconstruction technology may be used in radiological medical equipment to display images of various parts of a human body, that is, the computed tomography technology, or CT technology for short. And it may also be applied in other fields.

Image processing refers to the technology of analyzing an image with a computer to achieve a desired result. In the embodiments of the present application, it refers to perform image post-processing and signal extraction on a reconstructed result image to improve image clarity and highlight image features, and obtain a related parameter of a detected object, such as a velocity, a direction, an acceleration, a strain, a strain rate, an elastic modulus and other quantitative parameters of the detected object, etc.

Figure 1:
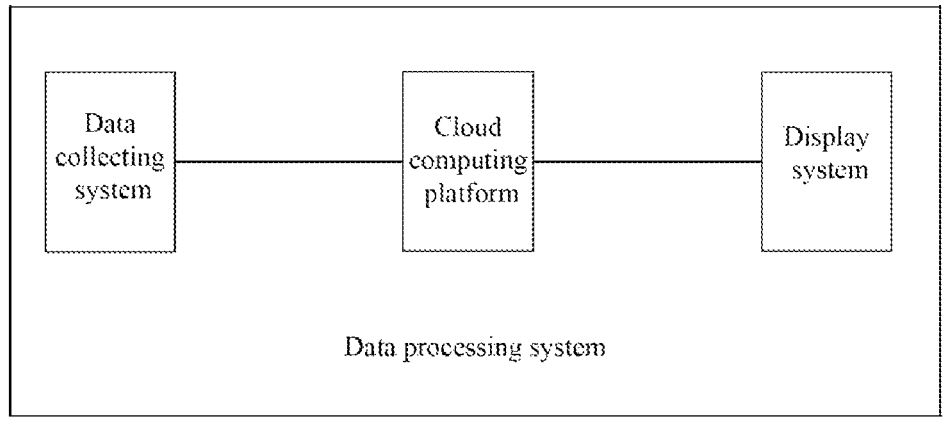
FIG. 1 is a schematic structural diagram of a data processing system to which an embodiment of the present application is applicable.

The data processing method provided by the embodiments of the present application is applicable to the following data processing system. As shown in FIG. 1, it is a schematic structural diagram of a data processing system to which an embodiment of the present application is applicable. The data processing system includes a cloud computing platform, a data collecting system and a display system. The data collecting system is responsible for collecting data to be processed, where the data to be processed may include a collected original ultrasonic echo signal. The cloud computing platform is responsible for performing corresponding processing on the data to be processed to obtain a required result. The display system is responsible for displaying related data or the result obtained during the processing of the cloud computing platform. The data processing system may also include a local computing platform for sharing part of processing tasks of the cloud computing platform.

The terms "first", "second", etc. are only used for descriptive purposes, and cannot be understood as indicating or implying relative importance or implicitly indicating a number of indicated technical features. In the description of the following embodiments, "multiple" means two or more, unless otherwise specifically defined.

The following specific embodiments can be combined with each other, and the same or similar concepts or processes may not be repeated in some embodiments. The embodiments of the present application will be described below in conjunction with the drawings.

Embodiment I

This embodiment provides a data processing method for processing an ultrasonic echo signal to obtain required result data. An execution subject of this embodiment is a data processing apparatus, which may be set in a cloud computing platform. Or the apparatus may be partly set in a local computing platform, and other parts are set in the cloud computing platform.

Figure 2:
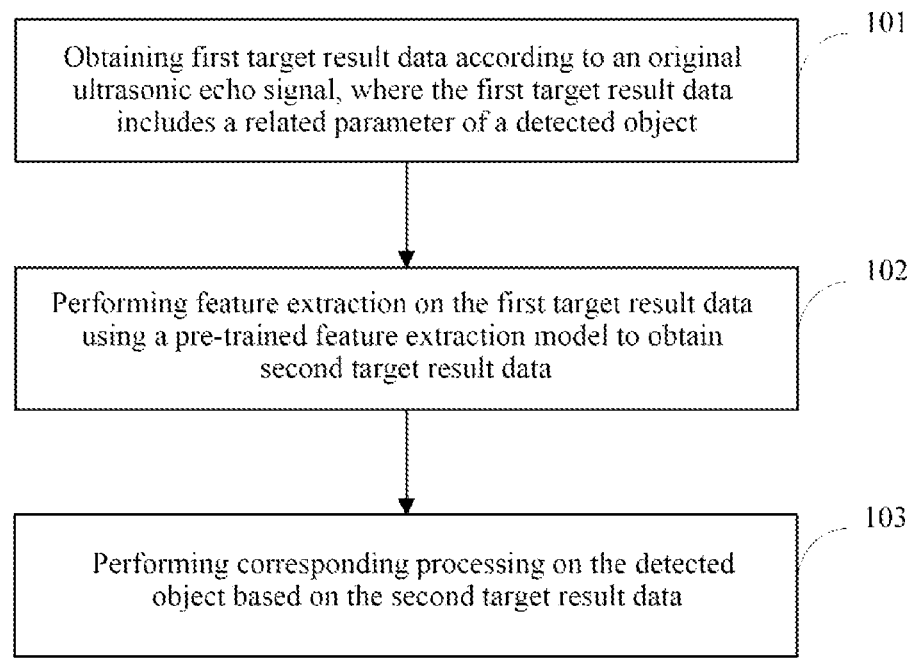
FIG. 2 is a schematic flowchart of a data processing method provided by an embodiment of the present application.

As shown in FIG. 2, it is a schematic flowchart of a data processing method provided by this embodiment, and the method includes:

step 101: obtaining first target result data according to an original ultrasonic echo signal, where the first target result data includes a related parameter of a detected object.

Specifically, the original ultrasonic echo signal may be obtained from a data collecting terminal, or may be collected and stored in advance, such as stored in a cloud computing platform, or stored in a local computing platform and sent to the cloud computing platform when needed for processing, or processed by the local computing platform, etc., and the specific obtaining method is not limited. After the original ultrasonic echo signal is acquired, the first target result data may be obtained according to the original ultrasonic echo signal, where the first target result data includes related parameters of the detected object, such as related parameters representing a moving velocity (such as a velocity of a blood flow), a moving direction (such as a direction of the blood flow), an elasticity (such as a strain, a strain rate, etc.) of the detected object, which may specifically include a displacement, a velocity, an acceleration, a strain, a strain rate, an elastic modulus and other quantitative parameters, etc. The first target result data may also include parameters related to image features, such as a contrast, a texture feature, and other quantitative parameters, and may also include information such as a distribution feature of scatterers, a density of the scatterers, and a size of the scatterers. There are no specific restrictions. The first target result data may be in a form of data or in a form of an image, such as a pseudo-color image.

The detected object may be human or animal tissues such as a liver, a kidney, a spleen, or other objects in the air or geology, which may be determined according to actual needs, and is not limited in the embodiment of the present application.

In an implementation, processing such as image reconstruction and image processing may be performed on the original ultrasonic echo signal to obtain the first target result data. The specific processing method may be the prior art, which is not limited in this embodiment.

Step 102, performing feature extraction on the first target result data using a pre-trained feature extraction model to obtain second target result data.

Specifically, the pre-trained feature extraction model may be a machine learning model or an artificial intelligence model, where the training of the feature extraction model may be performed using a large amount of pre-collected training data and labeled data obtained from labeling the training data. The specific training process is consistent with the training process of an existing neural network model, which will not be repeated here. Types of parameters included in the training data are consistent with those in the first target result data, such as different velocities of a blood flow, directions of a blood flow, and elasticity information. The labeled data may be texture features, uniformity, etc., or the labeled data may also be a state of the detected object corresponding to the training data, such as whether it is liver fibrosis, cirrhosis and its specific staging, whether it is fatty liver and its specific staging, whether it is tumor and benign or malignant. The detail may be set according to actual needs.

The trained feature extraction model may perform feature extraction and result prediction based on the first target result data to obtain the second target result data, where the second target result data may be an image texture feature, uniformity and other features of the detected object, and may also be a state feature of the detected object obtained after feature analysis and weighting of these features, such as whether the detected object is liver fibrosis, cirrhosis and its specific staging, fatty liver and its specific staging, tumor and benign or malignant, etc. Here, the state features output by the model may be labels corresponding to different states, for example, 0 means "normal", 1 means "fatty liver", etc., and the detail may be set according to actual needs, which is not limited in this embodiment.

In an implementation, at least two models such as a machine learning model and an artificial intelligence model may be used in parallel for feature extraction, and the results of each model are synthesized to obtain the second target result data. For example, three different models are used for feature extraction, if the state features of the detected object are acquired, where the results of two models are "1" and the result of one model is "0", the result should be "1" following the principle of "the minority is subordinate to the majority", however, this is only an exemplary description rather than a limitation.

Step 103, performing corresponding processing on the detected object based on the second target result data.

Specifically, after the second target result data is obtained, corresponding processing may be performed on the detected object based on the second target result data. For example, judging the state of the detected object based on the state feature of the detected object. For another example, displaying the state of the detected object, or displaying the second target result data of the detected object, etc. The second target result data may assist a related person to understand the state of the detected object. Such as assisting a doctor in diagnosis and so on.

In an implementation, the method provided in this embodiment may be executed by a cloud computing platform, or may be executed by a local computing platform, or partly executed by a local computing platform and partly executed by a cloud computing platform, and the detail may be set according to actual needs, which is not limited in this embodiment.

The data processing method provided in this embodiment, by performing feature extraction on the related parameter of the detected object using the pre-trained feature extraction model to obtain the second target result data, and further performing corresponding processing on the detected object based on the second target result data, combining the detection with a neural network, improves the judgment accuracy of the state of the detected object effectively.

Embodiment II

This embodiment further supplements the method provided in Embodiment I.

Figure 3:
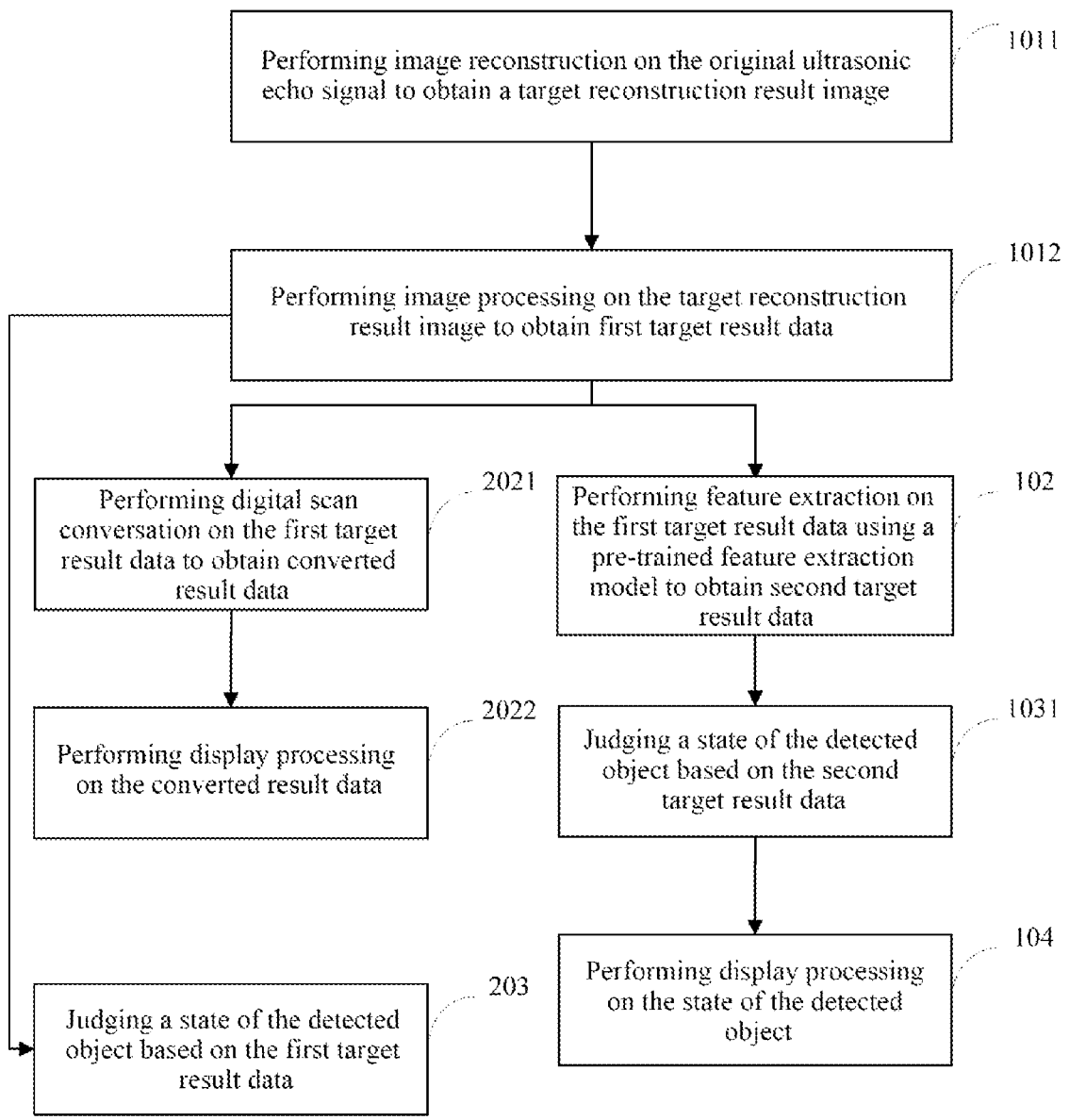
FIG. 3 is a schematic flowchart of a data processing method provided by another embodiment of the present application.

As shown in FIG. 3, it is a schematic flowchart of the data processing method provided by this embodiment.

As an implementable manner, on the basis of the above Embodiment I, in an implementation, step 101 specifically includes:

step 1011: performing image reconstruction on the original ultrasonic echo signal to obtain a target reconstruction result image.

Specifically, after the original ultrasonic echo signal is acquired, image reconstruction needs to be performed on the original ultrasonic echo signal to obtain the target reconstruction result image, such as an ultrasound image, a B-mode ultrasonic image, etc. The target reconstruction result image may be in the form of radio frequency, envelope, grayscale, etc.

Step 1012: performing image processing on the target reconstruction result image to obtain first target result data.

Specifically, after the target reconstruction result image is obtained, image processing needs to be performed on the target reconstruction result image to improve image clarity and highlight image features. For example, grayscale correction, grayscale expansion and compression, $\gamma$ correction, histogram equalization, electronic amplification, interpolation processing, etc., are performed. Finally, the related parameter of the detected object, that is, the first target result data is obtained. The specific image processing method may be set according to actual needs, which is not limited here.

In an implementation, step 1011 may specifically include:

step 10111: performing image reconstruction on the original ultrasonic echo signal using a spatial point-based image reconstruction algorithm to obtain a first reconstruction result image, where the spatial point-based image reconstruction algorithm is an image reconstruction algorithm compatible with multiple types of probes; and taking the first reconstruction result image as the target reconstruction result image.

In an implementation, the performing image reconstruction on the original ultrasonic echo signal using the spatial point-based image reconstruction algorithm to obtain the first reconstruction result image includes:

performing, according to pre-configured parameters of a probe and a display parameter, image reconstruction on the original ultrasonic echo signal using the spatial point-based image reconstruction algorithm to obtain the first reconstruction result image, where the parameters of the probe include an identifier of the probe, a Cartesian coordinate zero point of the probe, and a first coordinate of each array element of the probe, and the display parameter includes a second coordinate of the first reconstruction result image.

Specifically, the spatial point-based image reconstruction algorithm includes: pre-defined parameters of a probe, that is, a probe is defined in a unified format according to physical parameters of the probe to form a probe parameter index table, where the probe parameter index table is composed of an identification code of a type of the probe (i.e., the identifier of the probe), a Cartesian coordinate zero point of the probe and a coordinate position of each element of the probe (i.e., the first coordinate), a type of the probe currently used may be identified by the identification code, and the parameters of the probe may be searched in the probe parameter index table. In an implementation, a probe defining module may be set to manage the parameters of the probe. It is also necessary to define the display parameter of the reconstructed image, different display parameters may be defined for different types of probes, and image reconstruction is performed according to the display parameter, so as to be compatible with multiple types of probes. The display parameter is composed of a definition of a coordinate range, a coordinate position (Xi, Yi, Zi) or a pixel size ($\Delta$Xi, $\Delta$Yi, $\Delta$Zi) of a target image (that is, the target reconstruction result image). In an implementation, an image defining module may be set to manage the display parameter. A probe identifying module may also be set to identify the probe. The types of probe include linear array, convex array, phased array, two-dimensional area array and other types.

Due to different application scenarios of ultrasound probes, different types of probes have different shapes, sizes and response characteristics. In general, the probe is composed of multiple array elements, and the arrangement and size of the array elements have an impact on the image reconstruction algorithm.

During image reconstruction, the propagation path L(i) of ultrasound at any point P(i) (refers to a point corresponding to the coordinate position (Xi, Yi, Zi) in the above target image) in space is: $L(i)=L(t)+P(Xi,Yi,Zi)-P(Xt,Yt,Zt)$, $t=1, 2, 3 \ldots n$, $n \geq 1$, where n is the number of array elements of the probe. Furthermore, adaptive beam combination is realized (adaptation here refers to performing according to different coordinate requirements. The specific method may be an existing technology, such as delay overlaying, etc.). Among them, the coordinate zero point of the probe is a middle position of the probe (X0, Y0, Z0), the coordinate position of each element of the probe is (Xt, Yt, Zt), and a center plane of an imaging plane of the probe is the XZ plane, the plane which is perpendicular to the imaging plane of the probe and parallel to a tangent plane at the zero position of the probe is the XY plane.

Take the convex array probe as an example (not limited to the convex array probe): a position, a center frequency, a bandwidth and other parameters of the convex array probe are written into the probe defining module; a specific probe code is programed by using several pins of the convex array probe, the probe identifying module may identify the probe code when the probe is connected to the data processing system, and may further search the related parameters in the probe defining module; the display mode of the image (that is, the display parameter) is defined in the image defining module, and image reconstruction is performed according to such mode. This image reconstruction method is suitable for any probe, that is, it realizes ultrasound image reconstruction compatible with multiple types of probes, thereby improving the flexibility and efficiency of image reconstruction.

In some implementation manners, step 1012 may specifically include:

step 10121: performing image post-processing and signal extraction on the target reconstruction result image to obtain the first target result data, where the first target result data includes at least one of a displacement, a velocity, an acceleration, a strain, a strain rate, an elastic modulus, a contrast, a texture feature, a distribution feature of scatterers, a density of scatterers, and a size of scatterers.

Specifically, after the target reconstruction result image is obtained, image post-processing and signal extraction are performed on the target reconstruction result image to obtain the first target result data, such as Doppler, elasticity calculation, etc. If the above image reconstruction algorithm compatible with multiple types of probes is used in image reconstruction, the image processing may also be compatible with multiple types of probes, and the probe defining module, the probe identifying module, and the image defining module are still used. The probe identifying module identifies the type of the probe currently used by designing an identification code of the probe, and searches the parameters of the probe in the index table; the display parameter is defined in the image defining module, and image reconstruction is performed based on this parameter; and the image defining module performs image processing to obtain a data processing result (that is, the first target result data) that does not depend on the type of the probe, thereby realizing the compatibility of multiple types of probes.

Among them, image post-processing and signal extraction are the process of image processing, the image processing in this embodiment includes the whole process of image post-processing and signal extraction. For example, when a convex array is used for Doppler signal processing (a signal extraction method in the step of image processing), if a signal obtained by using a traditional image reconstruction algorithm is along an emission direction of the convex array (fan beam), when Doppler signal extraction is performed, the obtained direction of the blood flow is also along the emission direction of the convex array. If the distribution of the velocity of the blood flow in the horizontal or vertical direction in a Cartesian coordinate system is required, it can only be obtained by getting a component along a corresponding angle. While when adopting the image processing method in the embodiment of the present application, it is possible to directly obtain the distribution of the velocity of the blood flow in the horizontal or vertical direction in the Cartesian coordinate system (specifically, the distribution can be obtained by using autocorrelation, short time Fourier transform and other existing technologies based on the first target result data). In the same way, the method is also applicable to array elements of other types of probe, such as phased array and area array.

In some implementation manners, the performing image reconstruction on the original ultrasonic echo signal to obtain the target reconstruction result image includes:

in step 2011, for each probe, performing, according to an image reconstruction algorithm corresponding to a type of the probe, image reconstruction on the original ultrasonic echo signal to obtain a second reconstruction result image.

Specifically, image reconstruction is performed on each probe according to the respective image reconstruction algorithm configured to obtain the second reconstruction result image.

Here, a solution is provided when image reconstruction algorithms of multiple types of probes are not compatible, image reconstruction for each probe is performed according to the respective image reconstruction algorithm configured, that is, different types of probes may need to adopt different image reconstruction algorithms, a corresponding image reconstruction algorithm may be configured for a respective type of probe, and the image reconstruction algorithm corresponding to the probe is determined according to the type of the probe to perform image reconstruction after using different types of probes to collect the original ultrasonic echo signal. The specific reconstruction method is the existing technology, which will not be repeated here.

Step 2012: performing spatial interpolation processing on the second reconstruction result image to obtain a third reconstruction result image, and taking the third reconstruction result image as the target reconstruction result image.

Specifically, in order to obtain the target reconstruction result image compatible with different types of probes, it is necessary to perform spatial interpolation processing on the second reconstruction result image to obtain the third reconstruction result image which may be used as the target reconstruction result image.

The third reconstruction result image obtained through spatial interpolation processing is substantially equivalent to the first reconstruction result image obtained by the above spatial point-based image reconstruction algorithm. The difference is that the effects are slightly different, where the first reconstruction result image is obtained by direct reconstruction, and the third reconstruction result image is obtained by interpolating the traditional reconstruction result. Spatial interpolation processing may be implemented in a variety of ways, such as linear interpolation, non-linear interpolation and etc.

In an implementation, after the performing image processing on the target reconstruction result image to obtain the first target result data, the method may further include:

step 2021: performing digital scan conversation on the first target result data to obtain converted result data.

Step 2022: performing display processing on the converted result data.

Specifically, the obtained first target result data may also be used to assist in diagnosing and have certain reference significance. Therefore, the first target result data may be displayed, however, it needs to be displayed after digital scan conversion. Therefore, it is necessary to perform digital scan conversion on the first target result data to obtain the converted result data, and then perform display processing on the converted result data.

In some implementation manners, step 103 may specifically include:

step 1031: judging a state of the detected object based on the second target result data.

Exemplarily, judging, according to the second target result data, whether the detected object is liver fibrosis, cirrhosis and its specific staging, fatty liver and its specific staging, tumor and benign or malignant, etc.

In an implementation, the method may further include:

step 104: performing display processing on the state of the detected object.

In some implementation manners, after the obtaining the first target result data according to the original ultrasonic echo signal, the method further includes:

step 203: judging a state of the detected object based on the first target result data.

The obtained first target result data may also be used to assist in diagnosing and have certain reference significance, therefore, the state of the detected object may be judged based on the first target result data. For example, thresholds of different parameters and levels of the parameters may be set, where different levels correspond to different states of the detected object, etc., and the details will not be repeated here.

In some implementation manners, the method in the embodiment of the present application is executed by the cloud computing platform.

In other implementation manners, the local computing platform obtains the first target result data according to the original ultrasonic echo signal, and sends the first target result data to the cloud computing platform; the cloud computing platform performs feature extraction on the first target result data using the pre-trained feature extraction model to obtain the second target result data, and performs corresponding processing on the detected object based on the second target result data. That is, step 101 is executed by the local computing platform, and steps 102-103 are processed by the cloud computing platform.

It should be noted that each implementable manner in this embodiment can be implemented separately, or can be implemented in any combination without confliction, which is not limited in the present application.

The data processing method provided in this embodiment, by performing feature extraction on a related parameter of a detected object using a pre-trained feature extraction model to obtain the second target result data, and further performing corresponding processing on the detected object based on the second target result data, thereby improving accuracy of judging the state of the detected object effectively. Furthermore, by performing image reconstruction using a spatial point-based image reconstruction algorithm which can be compatible with multiple types of probes, thereby improving the flexibility and efficiency of image reconstruction. Furthermore, by performing image processing based on a target reconstruction result image compatible with multiple types of probes, thereby improving the accuracy of the related parameter of the detected object. Both the obtained first target result data and the second target result data may be used to assist a related person in diagnosing the detected object, thereby improving the diagnosis efficiency.

Embodiment III

This embodiment provides a data processing apparatus for executing the method in the above Embodiment I.

Figure 4:
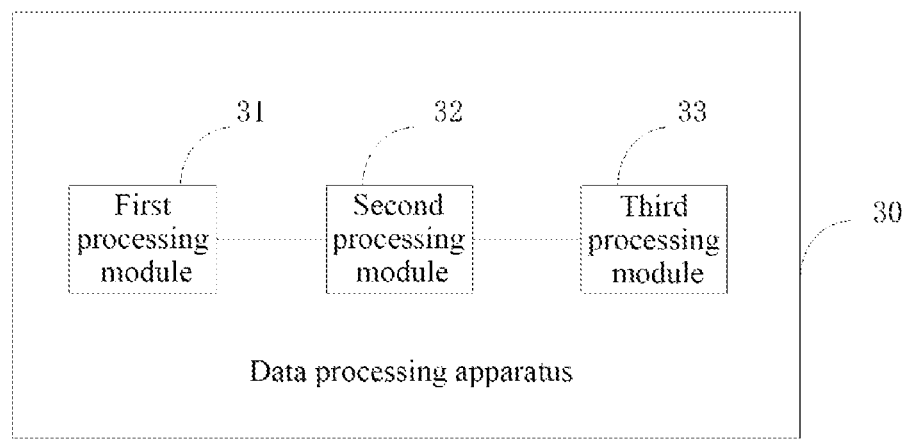
FIG. 4 is a schematic structural diagram of a data processing apparatus provided by an embodiment of the present application.

As shown in FIG. 4, it is a schematic structural diagram of a data processing apparatus provided by this embodiment. The data processing apparatus 30 includes a first processing module 31, a second processing module 32 and a third processing module 33.

Among them, the first processing module 31 is configured to obtain first target result data according to an original ultrasonic echo signal, where the first target result data includes a related parameter of a detected object; the second processing module 32 is configured to perform feature extraction on the first target result data using a pre-trained feature extraction model to obtain second target result data; and the third processing module 33 is configured to perform corresponding processing on the detected object based on the second target result data.

Regarding the apparatus in this embodiment, the specific manners for performing operations by each module have been described in detail in the embodiment related to the method, and detailed description will not be given here.

According to the data processing apparatus provided in this embodiment, by performing feature extraction on a related parameter of a detected object using a pre-trained feature extraction model to obtain second target result data, and further performing corresponding processing on the detected object based on the second target result data, thereby improving accuracy of judging the state of the detected object effectively.

Embodiment IV

This embodiment further supplements the apparatus provided in the above Embodiment III.

As an implementable manner, on the basis of the above embodiment III, in an implementation, the first processing module is specifically configured to:

perform image reconstruction on the original ultrasonic echo signal to obtain a target reconstruction result image; and perform image processing on the target reconstruction result image to obtain the first target result data.

In some implementation manners, the first processing module is specifically configured to:

perform image reconstruction on the original ultrasonic echo signal using a spatial point-based image reconstruction algorithm to obtain a first reconstruction result image, where the spatial point-based image reconstruction algorithm is an image reconstruction algorithm compatible with multiple types of probes; and take the first reconstruction result image as the target reconstruction result image.

In some implementation manners, the first processing module is specifically configured to:

perform, according to pre-configured parameters of a probe and a display parameter, image reconstruction on the original ultrasonic echo signal using the spatial point-based image reconstruction algorithm to obtain the first reconstruction result image; where the parameters of the probe include an identifier of the probe, a Cartesian coordinate zero point of the probe, and a first coordinate of each array element of the probe, and the display parameter includes a second coordinate of the first reconstruction result image.

In some implementation manners, the first processing module is specifically configured to:

perform image post-processing and signal extraction on the target reconstruction result image to obtain the first target result data, where the first target result data includes at least one of a displacement, a velocity, an acceleration, a strain, a strain rate, an elastic modulus, a contrast, a texture feature, a distribution feature of scatterers, a density of scatterers, and a size of scatterers.

In some implementation manners, the first processing module is specifically configured to:

perform, based on an image reconstruction algorithm which is not compatible with multiple types of probes, image reconstruction on the original ultrasonic echo signal to obtain a second reconstruction result image;

perform spatial interpolation processing on the second reconstruction result image to obtain a third reconstruction result image; and take the third reconstruction result image as the target reconstruction result image.

In an implementation, the first processing module is further configured to:

perform digital scan conversation on the first target result data to obtain converted result data; and perform display processing on the converted result data.

As another implementable manner, on the basis of the above Embodiment III, in an implementation, the third processing module is specifically configured to:

judge a state of the detected object based on the second target result data.

In some implementation manners, the third processing module is further configured to:

perform display processing on the state of the detected object.

As another implementable manner, on the basis of the above Embodiment III, in an implementation, the first processing module is further configured to judge a state of the detected object based on the first target result data.

Regarding the apparatus in this embodiment, the specific manners for performing operations by each module have been described in detail in the embodiment related to the method, and detailed description will not be given here.

It should be noted that each implementable manner in this embodiment can be implemented separately, or can be implemented in any combination without confliction, which is not limited in the present application.

According to the data processing apparatus of this embodiment, by performing feature extraction on a related parameter of a detected object using a pre-trained feature extraction model to obtain second target result data, and further performing corresponding processing on the detected object based on the second target result data, thereby improving accuracy of judging the state of the detected object effectively. Furthermore, by performing image reconstruction using a spatial point-based image reconstruction algorithm which can be compatible with multiple types of probes, thereby improving the flexibility and efficiency of image reconstruction. Furthermore, by performing image processing based on a target reconstruction result image compatible with multiple types of probes, thereby improving the accuracy of the related parameter of the detected object. Both the obtained first target result data and the second target result data may be used to assist a related person in diagnosing the detected object, thereby improving the diagnosis efficiency.

Figure 5:
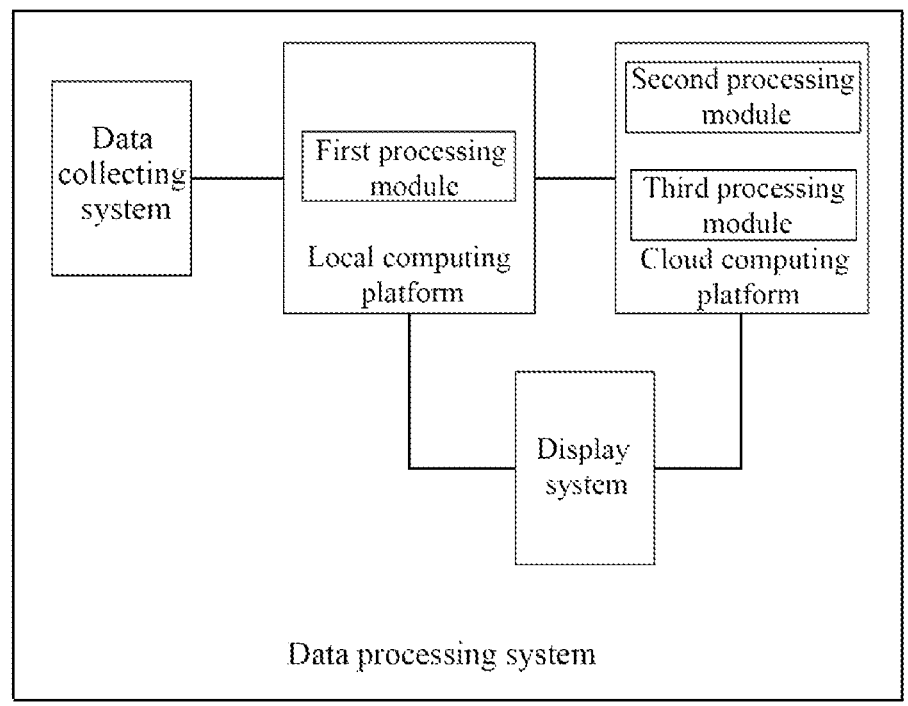
FIG. 5 is a schematic structural diagram of a data processing system provided by another embodiment of the present application.

In some embodiments, the data processing system may include a data collecting system, a local computing platform, a cloud computing platform, and a display system. As shown in FIG. 5, it is a schematic structural diagram of a data processing system provided by this embodiment. The first processing module in the data processing apparatus is set in a local computing platform, and the second processing module and the third processing module in the data processing apparatus are set in the cloud computing platform.

Embodiment V

This embodiment provides a computer device for executing the method provided in the above embodiment. The computer device may be the above cloud computing platform, or may include the above cloud computing platform and a local computing platform. Specifically, it may be a desktop computer, a notebook computer, a server, and other computer device.

Figure 6:
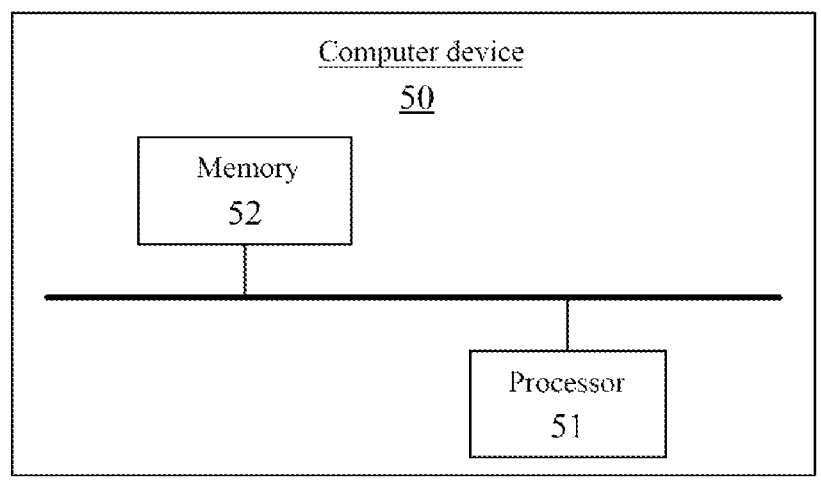
FIG. 6 is a schematic structural diagram of a computer device provided by an embodiment of the present application.

As shown in FIG. 6, it is a schematic structure diagram of the computer device provided by this embodiment. The computer device 50 includes: at least one processor 51 and a memory 52;

where the memory stores a computer program; and the at least one processor executes the computer program stored in the memory to implement the method provided in the above embodiments.

According to the computer device of this embodiment, by performing feature extraction on a related parameter of a detected object using a pre-trained feature extraction model to obtain second target result data, and further performing corresponding processing on the detected object based on the second target result data, thereby improving accuracy of judging the state of the detected object effectively. Furthermore, by performing image reconstruction using a spatial point-based image reconstruction algorithm which can be compatible with multiple types of probes, thereby improving the flexibility and efficiency of image reconstruction. Furthermore, by performing image processing based on a target reconstruction result image compatible with multiple types of probes, thereby improving the accuracy of the related parameter of the detected object. Both the obtained first target result data and the second target result data may be used to assist a related person in diagnosing the detected object, thereby improving the diagnosis efficiency.

Embodiment VI

This embodiment provides a computer-readable storage medium in which a computer program is stored, and the method provided in any of the above embodiments is implemented when the computer program is executed.

According to the computer-readable storage medium of this embodiment, by performing feature extraction on a related parameter of a detected object using a pre-trained feature extraction model to obtain second target result data, and further performing corresponding processing on the detected object based on the second target result data, thereby improving accuracy of judging the state of the detected object effectively. Furthermore, by performing image reconstruction using a spatial point-based image reconstruction algorithm which can be compatible with multiple types of probes, thereby improving the flexibility and efficiency of image reconstruction. Furthermore, by performing image processing based on a target reconstruction result image compatible with multiple types of probes, thereby improving the accuracy of the related parameter of the detected object. Both the obtained first target result data and the second target result data may be used to assist a related person in diagnosing the detected object, thereby improving the diagnosis efficiency.

In the several embodiments provided in the present application, it should be understood that the disclosed apparatus and method may be implemented in other ways. For example, the apparatus embodiments described above are merely illustrative, for example, the division of the units is only a logical function division, and there may be other divisions in actual implementation. For example, multiple units or components may be combined or integrated into another system, or some features may be omitted or not implemented. In addition, the displayed or discussed mutual coupling or direct coupling or communication connection may be indirect coupling or communication connection through some interfaces, apparatus or units, and may be in electrical, mechanical or other forms.

The units described as separate components may or may not be physically separated, and the components displayed as units may or may not be physical units, that is, they may be located in one place, or they may be distributed on multiple network units. Some or all of the units may be selected according to actual needs to achieve the objectives of the solutions of the embodiments.

In addition, the functional units in the various embodiments of the present application may be integrated into one processing unit, or each unit may exist alone physically, or two or more units may be integrated into one unit. The above integrated unit may be implemented in the form of hardware, or may be implemented in the form of hardware with a software functional unit.

The above integrated unit implemented in the form of a software functional unit may be stored in a computer readable storage medium. The above software functional unit is stored in the storage medium and includes several instructions to enable a computer device (which may be a personal computer, a server, or a network device, etc.) or a processor to execute a part of the steps of the method described in each embodiment of the present application. The above storage medium includes: a U disk, a portable hardisk, a read-only memory (ROM), a random access memory (RAM), a magnetic disk or an optical disk and other mediums that can store program codes.

The persons skilled in the art clearly understands that, the division of the above functional modules is only used as an example for the convenience and conciseness of the description. In practical applications, the above functions may be allocated by different functional modules according to needs, that is, the internal structure of the apparatus is divided into different functional modules to complete all or part of the functions described above. For the specific working process of the apparatus described above, reference may be made to the corresponding process in the above method embodiment, which will not be repeated here.

Finally, it should be noted that the above embodiments are only used to illustrate the technical solutions of the present application rather than limiting them; although the present application has been described in detail with reference to the above embodiments, the persons of ordinary skill in the art should understand that: it is still possible to modify the technical solutions recorded in the above embodiments, or equivalently replace some or all of the technical features; however, these modifications or replacements do not cause the essence of the corresponding technical solutions to deviate from the scope of the technical solutions of the embodiments of the present application.

What is claimed is:

1. A data processing method, executed by a data processing apparatus set in at least one of a cloud computing platform and a local computing platform, comprising:
receiving an original ultrasonic echo signal stored in at least one of the cloud computing platform and the local computing platform, obtaining first target result data according to the original ultrasonic echo signal, wherein the first target result data comprises a related parameter of a detected object, wherein the original ultrasonic echo signal is collected by one or more probes;
performing feature extraction on the first target result data using a pre-trained feature extraction model to obtain second target result data; and
performing corresponding processing on the detected object based on the second target result data;
wherein the obtaining the first target result data according to the original ultrasonic echo signal comprises:
performing image reconstruction on the original ultrasonic echo signal to obtain a target reconstruction result image; and
performing image processing on the target reconstruction result image to obtain the first target result data, wherein the image processing comprises at least one of grayscale correction, grayscale expansion and compression, γ correction, histogram equalization, electronic amplification and interpolation processing;
wherein the performing image reconstruction on the original ultrasonic echo signal to obtain the target reconstruction result image comprises:
when there is an image reconstruction algorithm compatible with different types of probes, performing image reconstruction on the original ultrasonic echo signal using a spatial point-based image reconstruction algorithm to obtain a first reconstruction result image, wherein the spatial point-based image reconstruction algorithm is the image reconstruction algorithm compatible with multiple types of probes; and
taking the first reconstruction result image as the target reconstruction result image;
wherein the performing image reconstruction on the original ultrasonic echo signal using the spatial point-based image reconstruction algorithm to obtain the first reconstruction result image comprises:
performing, according to pre-configured parameters of a probe and a display parameter, image reconstruction on the original ultrasonic echo signal using the spatial point-based image reconstruction algorithm to obtain the first reconstruction result image, wherein the parameters of the probe comprise an identifier of the probe, a Cartesian coordinate zero point of the probe, and a first coordinate of each array element of the probe, and the display parameter comprises a second coordinate of the first reconstruction result image;
wherein the image reconstruction is based on a propagation path $L(i)$ of a point $P(i)$ corresponding to the target reconstruction result image, wherein $L(i)=L(t)+P(X_i, Y_i, Z_i)-P(X_t, Y_t, Z_t)$, $t=1,2,3 \ldots n$, $n \geq 1$, $n$ is a number of array elements of the probe, $(X_t, Y_t, Z_t)$ is the first coordinate of each element of the probe, and $(X_i, Y_i, Z_i)$ is the second coordinate of the first reconstruction result image.

2. The method according to claim 1, wherein the performing image processing on the target reconstruction result image to obtain the first target result data comprises:
performing image post-processing and signal extraction on the target reconstruction result image to obtain the first target result data, wherein the first target result data comprises at least one of a displacement, a velocity, an acceleration, a strain, a strain rate, an elastic modulus, a contrast, a texture feature, a distribution feature of scatterers, a density of scatterers, and a size of scatterers.

3. The method according to claim 1, wherein the performing image reconstruction on the original ultrasonic echo signal to obtain the target reconstruction result image further comprises:
when image reconstruction algorithms of different types of probes are not compatible, for each probe of the one or more probes, performing, according to an image reconstruction algorithm corresponding to a type of the probe, image reconstruction on the original ultrasonic echo signal to obtain a second reconstruction result image;
performing spatial interpolation processing on the second reconstruction result image to obtain a third reconstruction result image; and
taking the third reconstruction result image as the target reconstruction result image.

4. The method according to claim 3, wherein after the performing image processing on the target reconstruction result image to obtain the first target result data, the method further comprises:
performing digital scan conversation on the first target result data to obtain converted result data; and
performing display processing on the converted result data.

5. The method according to claim 1, wherein the performing corresponding processing on the detected object based on the second target result data comprises:
judging a state of the detected object based on the second target result data.

6. The method according to claim 5, further comprising:
performing display processing on the state of the detected object.

7. The method according to claim 1, wherein after the obtaining the first target result data according to the original ultrasonic echo signal, the method further comprises:
judging a state of the detected object based on the first target result data.

8. A computer device, comprising: at least one processor and a memory;
wherein the memory stores a computer program; and the at least one processor executes the computer program stored in the memory to:
obtain first target result data according to an original ultrasonic echo signal, wherein the first target result data comprises a related parameter of a detected object, wherein the original ultrasonic echo signal is collected by one or more probes;
perform feature extraction on the first target result data using a pre-trained feature extraction model to obtain second target result data; and
perform corresponding processing on the detected object based on the second target result data;
wherein the at least one processor is specifically configured to:
perform image reconstruction on the original ultrasonic echo signal to obtain a target reconstruction result image; and
perform image processing on the target reconstruction result image to obtain the first target result data, wherein the image processing comprises at least one of grayscale correction, grayscale expansion and compression, γ correction, histogram equalization, electronic amplification and interpolation processing;
wherein the at least one processor is specifically configured to:
when there is an image reconstruction algorithm compatible with different types of probes, perform image reconstruction on the original ultrasonic echo signal using a spatial point-based image reconstruction algorithm to obtain a first reconstruction result image, wherein the spatial point-based image reconstruction algorithm is an image reconstruction algorithm compatible with multiple types of probes; and
take the first reconstruction result image as the target reconstruction result image;
wherein the at least one processor is specifically configured to:
perform, according to pre-configured parameters of a probe and a display parameter, image reconstruction on the original ultrasonic echo signal using the spatial point-based image reconstruction algorithm to obtain the first reconstruction result image; wherein the parameters of the probe comprise an identifier of the probe, a Cartesian coordinate zero point of the probe, and a first coordinate of each array element of the probe, and the display parameter comprises a second coordinate of the first reconstruction result image;
wherein the image reconstruction is based on a propagation path $L(i)$ of a point $P(i)$ corresponding to the target reconstruction result image, wherein $L(i)=L(t)+P(Xi, Yi, Zi)-P(Xt, Yt, Zt)$, $t=1,2,3 \ldots n$, $n \geq 1$, n is a number of array elements of the probe, $(Xt, Yt, Zt)$ is the first coordinate of each element of the probe, and $(Xi, Yi, Zi)$ is the second coordinate of the first reconstruction result image.

9. The device according to claim 8, wherein the at least one processor is specifically configured to:
perform image post-processing and signal extraction on the target reconstruction result image to obtain the first target result data, wherein the first target result data comprises at least one of a displacement, a velocity, an acceleration, a strain, a strain rate, an elastic modulus, a contrast, a texture feature, a distribution feature of scatterers, a density of scatterers, and a size of scatterers.

10. The device according to claim 8, wherein the at least one processor is further configured to:
when image reconstruction algorithms of different types of probes are not compatible, for each probe of the one or more probes, perform, according to an image reconstruction algorithm corresponding to a type of the probe, image reconstruction on the original ultrasonic echo signal to obtain a second reconstruction result image;
perform spatial interpolation processing on the second reconstruction result image to obtain a third reconstruction result image; and
take the third reconstruction result image as the target reconstruction result image.

11. The device according to claim 10, wherein the at least one processor is further configured to:
perform digital scan conversation on the first target result data to obtain converted result data; and
perform display processing on the converted result data.

12. The device according to claim 8, wherein the at least one processor is specifically configured to:
judge a state of the detected object based on the second target result data.

13. The device according to claim 12, wherein the at least one processor is further configured to:
perform display processing on the state of the detected object.

14. A non-transitory computer-readable storage medium, wherein a computer program is stored in the non-transitory computer-readable storage medium, and the computer program, when executed, cause a computer to:

obtain first target result data according to an original ultrasonic echo signal, wherein the first target result data comprises a related parameter of a detected object, wherein the original ultrasonic echo signal is collected by one or more probes;

perform feature extraction on the first target result data using a pre-trained feature extraction model to obtain second target result data; and perform corresponding processing on the detected object based on the second target result data;

wherein the computer program, when executed, cause the computer further to:

perform image reconstruction on the original ultrasonic echo signal to obtain a target reconstruction result image; and perform image processing on the target reconstruction result image to obtain the first target result data, wherein the image processing comprises at least one of grayscale correction, grayscale expansion and compression, γ correction, histogram equalization, electronic amplification and interpolation processing;

wherein the computer program, when executed, cause the computer further to:

when there is an image reconstruction algorithm compatible with different types of probes, perform image reconstruction on the original ultrasonic echo signal using a spatial point-based image reconstruction algorithm to obtain a first reconstruction result image, wherein the spatial point-based image reconstruction algorithm is an image reconstruction algorithm compatible with multiple types of probes; and take the first reconstruction result image as the target reconstruction result image;

wherein the computer program, when executed, cause the computer further to:

perform, according to pre-configured parameters of a probe and a display parameter, image reconstruction on the original ultrasonic echo signal using the spatial point-based image reconstruction algorithm to obtain the first reconstruction result image; wherein the parameters of the probe comprise an identifier of the probe, a Cartesian coordinate zero point of the probe, and a first coordinate of each array element of the probe, and the display parameter comprises a second coordinate of the first reconstruction result image;

wherein the image reconstruction is based on a propagation path $L(i)$ of a point $P(i)$ corresponding to the target reconstruction result image, wherein $L(i)=L(t)+P(X_i, Y_i, Z_i)-P(X_t, Y_t, Z_t)$, $t=1,2,3 \ldots n$, $n \geq 1$, n is a number of array elements of the probe, $(X_t, Y_t, Z_t)$ is the first coordinate of each element of the probe, and $(X_i, Y_i, Z_i)$ is the second coordinate of the first reconstruction result image.

* * * * *